June 16, 1964
E. S. BOERNER
Plant Pat. 2,411
ROSE PLANT
Filed June 26, 1963
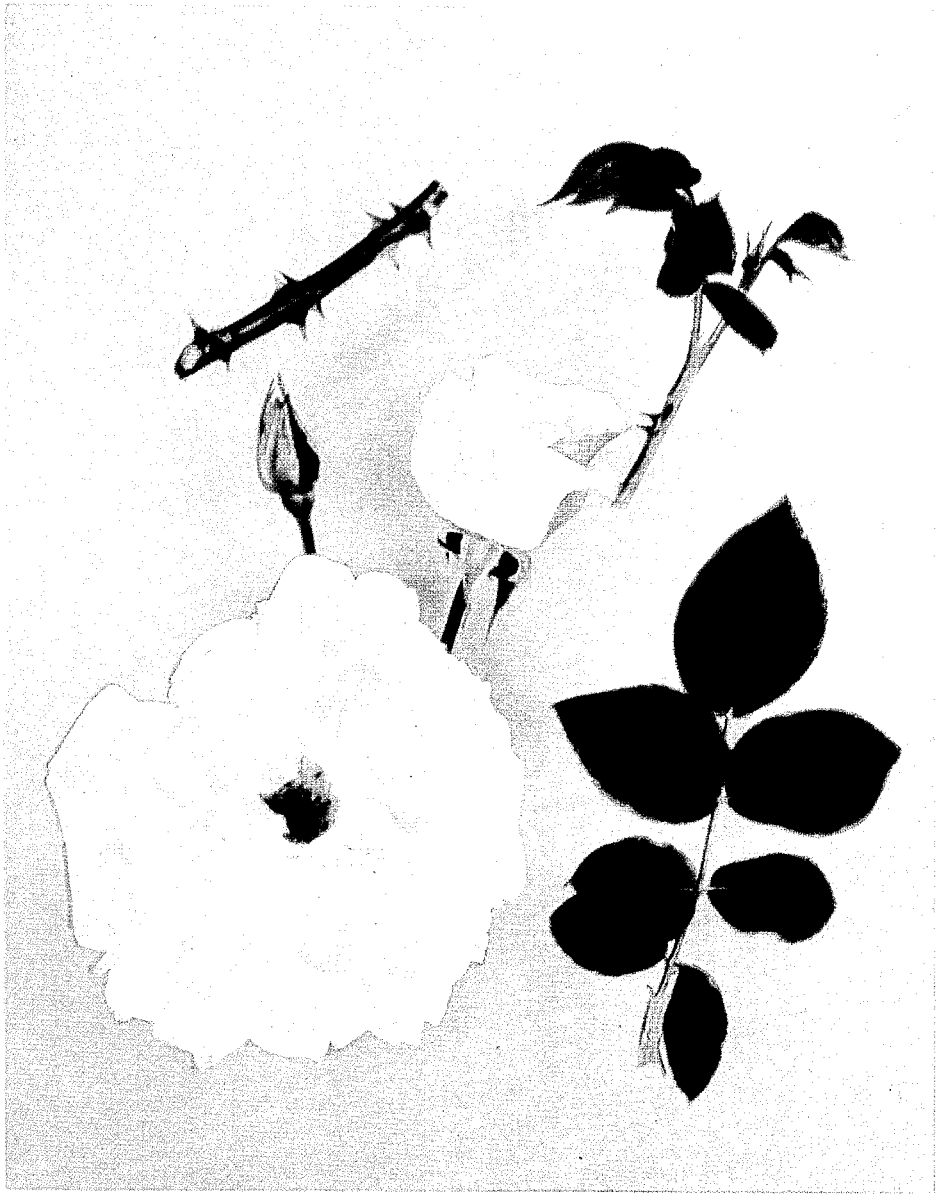
Inventor.
E. S. Boerner
By: Robb & Robb
Attorneys.

United States Patent Office

Plant Pat. 2,411
Patented June 16, 1964

2,411
ROSE PLANT

Eugene S. Boerner, Newark, N.Y., assignor to Jackson & Perkins Company, Newark, N.Y., a corporation of New York Filed June 26, 1963, Ser. No. 290,875
1 Claim. (Cl. Plt.—26)

The present invention relates to a new and distinct variety of rose plant of the floribunda class, which was originated by me by crossing an unnamed and unpatented very double seedling of "White Garnette" (Plant Patent No. 1,225) with the variety "Hawaii" (Plant Patent No. 1,833).

The primary objective of this breeding was to combine the "Hawaii" flower color with a stiff petaled floribunda flower habit, while at the same time increasing the flower petalage to make the flowers more double than those of the parent variety "Hawaii." This objective was fully achieved, along with other desirable improvements, as evidenced by the following unique combination of characteristics which are outstanding in the new variety and which distinguish it from its parents, as well as from all other varieties of which I am aware:

(1) A large flowered floribunda habit;

(2) A graceful flower opening habit, with the flowers finishing flat, but with the center petals upright;

(3) Leathery and firm flower petals; and (4) A distinctive and attractive general color tonality of the flowers corresponding to Geranium Pink, lightly overcast with Begonia Rose.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed very double seedling of "White Garnette."

*Pollen parent.*—"Hawaii."

Classification:

*Botanic.*—Floribunda.

*Commercial.*—Floribunda.

*Flower*

(Observations made from specimens grown outdoors at Newark, New York, in the early morning during the middle part of the month of September.)

Blooming habit: Recurrent—continuous.

Bud:

*Size.*—Large.

*Form.*—Ovoid; is not affected by wet or hot weather.

*Color.*—When sepals first divide — Eugenia Red, Plate 13. When petals begin to unfurl — Rose Doree, Plate 1. When half-blown: inside of petals—Begonia Rose, Plate 1, very lightly overcast with Grenadine Red, Plate 2 on the outer edges of the petals; reverse of petals—Begonia Rose, Plate 1, very lightly overcast with Rose Red, Plate 12.

*Sepals.*—Branched; curl back when petals begin to unfurl. Color: inside—Light Turtle Green, Plate 32, with edges of sepals lightly overcast with Pomegranate Purple, Plate 12; outside — Light Bice Green, Plate 17, lightly overcast with Oxblood Red, Plate 1.

*Calyx.* — Color — Light Bice Green, Plate 17. Shape — pear. Size — small. Aspect — smooth. Odor when rubbed—none.

*Peduncle.*—Length — medium. Aspect — smooth. Strength—erect; heavy. Color—Light Elm Green, Plate 17.

*Opening.*—Opens up well; is not affected by adverse weather conditions.

Bloom:

*Size.* — Medium. Average size when fully expanded—4¾ inches.

*Borne.*—Both singly and in irregular clusters.

*Stems.*—Medium length; strong.

*Form (when first open).*—High-centered. Permanence—finishes flat, with the center petals upright.

*Petalage.*—Double (full but open center). Number of petals under normal conditions—40.

*Color.* — Center of flower — Rose Doree, Plate 1. Outer petals—Eosine Pink, Plate 1, with edges of petals overcast with Begonia Rose, Plate 1. Base of petals (aiglet)—Light Orange Yellow, Plate 3. Inside of petals—Grenadine Pink, Plate 1, lightly overcast with Begonia Rose, Plate 1. Reverse of petals—Eosine Pink, Plate 1. General tonality from a distance—Geranium Pink, Plate 1, lightly overcast with Begonia Rose, Plate 1.

*Discoloration.*—General tonality at end of first day—Rose Doree, Plate 1. Second day—Rose Doree, Plate 1, lightly overcast with Geranium Pink, Plate 1. Third day—Geranium Pink, Plate 1, very lightly overcast with Begonia Rose, Plate 1.

Petals:

*Texture.*—Leathery; firm; is not affected by wet or hot weather.

*Appearance.*—Inside—satiny. Outside—shiny.

*Form.*—Oval; slightly notched.

*Arrangement.* — Imbricated (regularly arranged shingle-like).

*Pentaloids in center.*—Few; small.

*Persistence.*—Drop off cleanly.

*Fragrance.*—Moderate. Nature—tea (average hybrid tea scent).

*Lasting quality.* — On the plant — long. As cut flower—long.

*Genital Organs*

Stamens, anthers: Medium size; many; regularly arranged around styles. Color—Orange-Buff, Plate 3.

Stamens, filaments (threads): Medium length. Color—Orient Pink, Plate 2.

Pollen: Color—Pale Yellow-Orange, Plate 3.

Styles: Bunched; uneven length; medium length; thin.

Stigmas: Color—Capucine Buff, Plate 3.

Ovaries: All enclosed in calyx.

Hips: None.

Seeds: None.

Form: Bush.

Growth: Vigorous; upright.

Foliage: Compound of 5–7 leaflets.

*Size.*—Medium.

*Quantity.*—Normal.

*Color.*—New foliage: upper side—Morocco Red, Plate 1; under side—Oxblood Red, Plate. 1. Old foliage: upper side — Forest Green, Plate 18; under side—Biscay Green, Plate 17.

*Shape.*—Oval pointed.

*Texture.*—Upper side—glossy. Under side—smooth.

*Ribs and veins.*—Ordinary.

*Edge.*—Slightly serrated (saw-toothed).

*Serration.*—Both double and single; small.

*Leaf stem.*—Color—Courge Green, Plate 17, lightly overcast with Acajou Red, Plate 13. Under side—prickly.

*Stipules.*—Short; smooth.

Wood:

*New wood.*—Color—Light Yellowish Olive, Plate 30. Bark—smooth.

*Old wood.*—Color—Spinach Green, Plate 5. Bark—smooth.

Thorns:

*Thorns.*—Quantity: on main stalks from base—ordinary; on laterals from stalk—ordinary. Form—narrow base; medium length; some straight and some hooked downward. Color (when young)—Bordeaux, Plate 12. Position—irregular.

*Prickles.*—Quantity: on main stalks—none; on laterals—none.

*Short needles.*—Quantity: on main stalks—none; on laterals—none.

I claim:

A new and distinct variety or rose plant of the floribunda class, substantially as herein shown and described, characterized particularly as to novelty by the unique combination of a large flowered floribunda habit, a graceful flower opening habit, with the flowers finishing flat but with the center petals upright, leathery and firm flower petals, and a distinctive and attractive general color tolality of the flowers corresponding to Geranium Pink, lightly overcast with Begonia Rose.

No references cited.